United States Patent [19]

Fixel

[11] 4,120,298
[45] Oct. 17, 1978

[54] IMPLANT TO SECURE THE GREATER TROCHANTER

[76] Inventor: Irving E. Fixel, 111 N. 31 Ave., Hollywood, Fla. 33021

[21] Appl. No.: 748,234

[22] Filed: Dec. 6, 1976

[51] Int. Cl.² .................. A61F 5/04; A61B 17/18
[52] U.S. Cl. .................. 128/92 D; 128/92 B; 128/92 BA
[58] Field of Search .......... 128/92 B, 92 R, 92 BA, 128/92 BB, 92 BC, 92 D, 92 G, 92 C, 92 CA; 3/1.912, 1.913

[56] References Cited

U.S. PATENT DOCUMENTS

| | | | |
|---|---|---|---|
| 2,631,584 | 3/1953 | Purificato | 128/92 BA |
| 2,699,774 | 1/1955 | Livingston | 128/92 BB |
| 3,002,514 | 10/1961 | Deyerle | 128/92 EB |
| 3,824,995 | 7/1974 | Getscher et al. | 128/92 B |
| 3,842,825 | 10/1974 | Wagner | 128/92 B X |

FOREIGN PATENT DOCUMENTS

| | | | |
|---|---|---|---|
| 960,010 | 10/1942 | France | 128/92 B |
| 2,289,154 | 5/1976 | France | 128/92 BA |
| 491,382 | 2/1976 | U.S.S.R. | 128/92 BA |

*Primary Examiner*—Ronald L. Frinks
*Attorney, Agent, or Firm*—Richard M. Saccocio

[57] ABSTRACT

A bone implant fixation plate having an angled bend intermediate its ends provides improved structure for fixation of the greater trochanter to the femur. Hollow pins are fixed to the intermediate bend for fixation in drilled holes in the greater trochanter by a flaring tool.

5 Claims, 1 Drawing Figure

IMPLANT TO SECURE THE GREATER TROCHANTER

BACKGROUND TO THE INVENTION

1. Field of the Invention

This innovation deals with a new artifical implant used in a hip joint surgery. This bone fixation device is designed to strengthen and to secure the greater trochanter when resected.

2. Description of Prio Art

The conventional technique to attach and secure the greater trochanter to the femur as part of a hip joint surgery is by the use of tie wires or sometimes screws. Since the quality of this bony section of the femur is considered rather weak and fragile and the fact that a substantial muscle-pull must be balanced by this fixation the wires or screws used often prove to be insufficient to take the loads imposed. As a result of this, the wires or screws may damage the bone, break or displace the bone before it has a chance to heal and carry the loads without assistance. As a secondary effect, separated portions of the broken wires may interfere with the hip joint function. Also dislocation of the hip joint is often resulted by the breakage of the tie wires.

BRIEF DESCRIPTION OF THE INVENTION

The main purpose of this invention is to provide means to reinforce and securely fasten the greater trochanter to the femur.

Also another object of this invention is to prevent postoperative damages previously experienced by using traditional methods.

DETAILED DESCRIPTION OF THE PREFERRED EMBODIMENT

Figure 1:
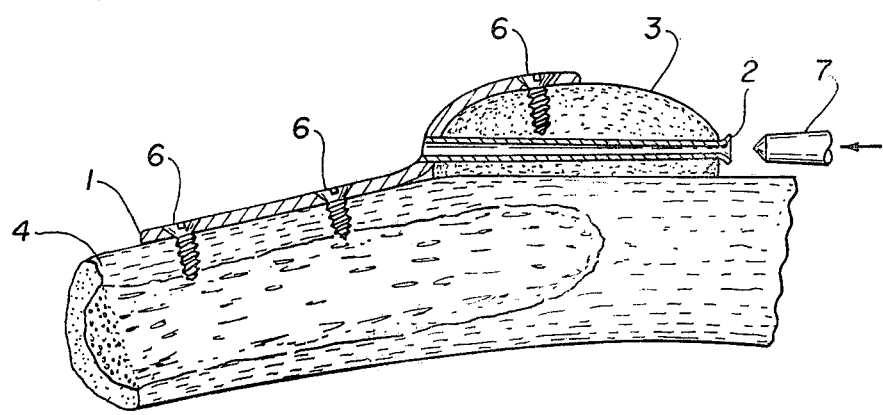
FIG. 1 illustrates the implant as applied to the femur showing the method of fixing and locating the greater trochanter to the femur.
Figure 2:
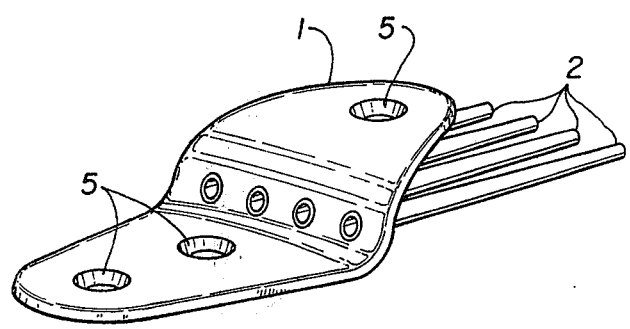
FIG. 2 is an isometric view of the implant of FIG. 1 showing the details of the invention.

The implant as illustrated in FIG. 1 is constructed to conform with the shape of the femur and greater trochanter. The larger component part is the plate 1. Said plate 1 is formed of a slender material. A number of parallel hollow pins 2 are attached at about the midsection of said plate 1. One end of the plate 1 is formed to approximate the upper curvature of the greater trochanter 3 and the other end is fitted flush to the femur 4. Holes 5 are provided to accept screw type fasteners 6 to anchor the implant in place. The hollow pins 2 are either of cylindrical or of conical shape. Matching holes are drilled through the greater trochanter to fix and accept the pins 2. An appropriate drill jig may be used to assure accuracy of hole locations. The exposed end of the pins 2 are slotted and flared by a tapered flaring tool 7 in order to immobilize the implant relative to the bone. The implant is fastened to the bone by screw type fasteners 6. The inside holes through the pins 2 may be used to guide tie wires if so required.

What is claimed is:

1. A bone implant fixation device for support and fixation of the greater trochanter to the femur by implantation in skeletal bone, comprising
   a plate member, comprising a thin metal plate having a first portion which is adapted to fit over the exterior surface of the femur shaft and a second portion adapted to fit over the exterior surface of the trochanter, said first and second portions having a bend therebetween, said bend being adapted to extend across the meeting ends of the trochanter and the femur shaft and to space apart said first portion and said second portion of the plate member in substantially parallel planes,
   a plurality of hollow pin members attached to said plate member at the location of said bend such that said pin members extend from said plate in a plane which is substantially parallel to the plane of said second portion of said plate,
   fastener means extending through said plate member adapted to secure said implant device to skeletal bone to which the implant device is to be applied.

2. The device of claim 1 wherein said pin members have a length which is adapted to extend through mating holes in the trochanter and extend therefrom a short distance, said pin members being flared at their ends remote from the attachment to said plate member said flare being adapted to firmly attach said implant device to the trochanter.

3. The device of claim 1 wherein said plurality of pin members numbers four.

4. The device of claim 1 wherein said plate member includes a plurality of holes extending therethrough said holes being adapted to receive said fastener means comprising screws to fasten said device to the femur and the trochanter.

5. The device of claim 1 wherein said pin members are tapered with the larger size of said taper being located at the attachment end of said pin member to said plate member and the smaller size of said taper being located at the end remote from the attachment end.

* * * * *